United States Patent [19]

Lehrer

[11] 4,351,824

[45] Sep. 28, 1982

[54] POLYSTYRENE LATEX REAGENTS, METHODS OF PREPARATION, AND USE IN IMMUNOLOGICAL PROCEDURES

[75] Inventor: Harris I. Lehrer, Long Beach, Calif.

[73] Assignee: ICL Scientific, Fountain Valley, Calif.

[21] Appl. No.: 231,683

[22] Filed: Feb. 5, 1981

[51] Int. Cl.³ .................. G01N 33/54; G01N 33/68
[52] U.S. Cl. ........................ 424/12; 23/230 B; 260/121; 424/8; 424/13; 424/78; 523/205; 524/20; 524/21; 524/18
[58] Field of Search ................ 424/8, 12, 13, 78; 23/230 B; 260/6, 8, 121

[56] References Cited

U.S. PATENT DOCUMENTS

| | | | |
|---|---|---|---|
| 3,088,875 | 5/1963 | Fisk | 424/12 |
| 3,551,555 | 12/1970 | Schuurs | 424/12 |
| 3,658,982 | 4/1972 | Reiss | 424/12 |
| 3,666,421 | 5/1972 | Price | 424/12 X |
| 3,826,613 | 7/1974 | Parikh | 424/12 |
| 3,992,517 | 11/1976 | Lowke | 424/12 |
| 4,181,636 | 1/1980 | Fischer | 424/12 X |
| 4,234,563 | 11/1980 | Rippe | 424/8 |

FOREIGN PATENT DOCUMENTS 1914081  10/1970  Fed. Rep. of Germany .

OTHER PUBLICATIONS

Plescia, Methods in Enzymology; vol. 12, 1968, (Grossman et al. Ed) Academic Press, N.Y., pp. 893–899.
Talal, et al., Manual for Antibodies to Deoxyribonucleic Acid, Am. Soc. for Microbiol., 1st ed., 1976, pp. 652–655.
Plescia et al., Biochem., vol. 52, 1964, pp. 279–285.
Sasaki, et al., J. Immunol. Methods, vol. 22, 1978, pp. 327–337.
Gabrilovas et al., J. Immunol. Methods, vol. 30, 1979, pp. 161–170.
Christian, PSEBM, vol. 98, 1958, pp. 820–823.

*Primary Examiner*—Anna P. Fagelson
*Attorney, Agent, or Firm*—Fulwider, Patton, Rieber, Lee & Utecht

[57] ABSTRACT

Methods of making and using a stable diagnostic reagent for use in serological testing procedures, and in particular, non-auto-agglutinating polystyrene latex particles with surfaces containing a protein, substantially methylated serum albumin, and a bound, negatively-charged polymeric compound. The particles may be sensitized with a number of negatively-charged compounds, including proteins, polysaccharides and various cell nuclear components. When the coated latex particles are adsorbed with native deoxyribonucleic acid, the resultant immunological reagent can be used to detect certain autoimmune diseases, particularly serum lupus erythematosus.

30 Claims, No Drawings

POLYSTYRENE LATEX REAGENTS, METHODS OF PREPARATION, AND USE IN IMMUNOLOGICAL PROCEDURES

BACKGROUND OF THE INVENTION

The present invention relates generally to a reagent and method for the in vitro diagnosis of diseases, and more particularly, to coated polystyrene latex particles and their use in agglutination procedures for serological testing. This invention also relates to the diagnosis of the human autoimmune diseases, particularly the collagen or rheumatic diseases.

Upon infection by foreign matter of antigenic character, many animals exhibit an immunologic response. One aspect of this response is the presence in the animal's blood of antibodies, so-called circulating antibodies, capable of recognizing and binding the foreign material.

The animal's ability to distinguish its own organic matter from unwanted foreign material is obviously a preeminent feature of the immune response. Unfortunately, for reasons not completely understood, this failsafe mechanism against self-reactivity sometimes breaks down, initiating a pathological state in the animal due to the presence of self-reactive, circulating antibodies. Indeed, the presence of self-reactive antibodies has been connected with an increasing number of diseases, such as hemolytic anemia, hyperthyroidism, thyroiditis, Sjorgren's syndrome, rheumatoid arthritis, polymyositis, scleroderma and systemic lupus erythematosus.

This latter group of five diseases, known as collagen or rheumatic diseases, has a number of common traits. Patients suffering from these diseases often exhibit circulating antibodies to a number of cell components. Of particular interest to clinicians are the antibodies directed against nuclear components, such as native deoxyribonucleic acid (native DNA), denatured deoxyribonucleic acid, deoxyribonucleoprotein, histones, Sm antigen, and ribonucleoprotein. These are believed to play a central role in the pathological condition.

A number of tests have been developed to detect circulating antibodies against nuclear materials. Perhaps the oldest of these tests is the LE cell preparation, a test exhibiting specificity for antideoxyribonucleoprotein. The LE cell preparation is positive with only about 70% of sera from active systemic lupus erythematosus patients, and is also positive in some sera of patients with drug-induced lupus syndromes, rheumatoid arthritis, other chronic connective tissue diseases, and chronic active hepatitis. Laboratory technicians basically consider the LE cell test tedious and generally unsuited for large scale screening.

For these reasons and others, the LE cell preparation has been replaced, to a large extent, by the indirect immunofluorescent anti-nuclear antibody (ANA) test, especially for routine testing purposes. The immunofluorescent ANA test can utilize a number of different substrates, because the components materials tested for, antinuclear antibodies, react with a variety of substrates. Four primary patterns of nuclear fluorescence, which apparently result from the presence of circulating antibodies directed against the various nuclear components, have been distinguished and must be recognized during testing. This complexity has introduced the need for technical expertise and expensive hardware to avoid making errors during the interpretation of test results.

Several other methods for the routine analysis of antibodies to individual nuclear components, including native DNA antibodies are also available. One DNA specific method incorporates the Farr ammonium sulfate globulin-precipitation technique and utilizes enzymes, fluorescence, or more commonly, radioactivity to label native DNA. To obtain reproduceable results, this procedure requires very careful attention to technique. A second DNA specific method is another immunofluorescent technique, which although utilizing the kinetoplast of the flagellate *Crithidia lucillae* as substrate, still shares many of the difficulties of the immunofluorescent ANA test. An additional procedure, the passive hemagglutination test, has also been developed, but its utility is somewhat curtailed due to the relative instability of the red blood cell carrier and the need for frequent recalibrations.

Much effort to improve the diagnostic process for detecting the rheumatic type of autoimmune disease has centered around the agglutination of latex particles. The practicality of latex reagents in diagnostic procedures has been known for a number of years, and by way of example, several latex procedures and reagents can be found in U.S. Pat. Nos. 3,088,875, 3,658,982, 3,826,613, 3,992,517, and German Pat. No. 1,914,081. Generally, a workable latex agglutination procedure should be reproducible, sensitive, suitable for large-scale screening, and relatively specific; and the latex particles should not autoagglutinate under routine storage conditions. A more effective latex reagent meeting these requirements is needed for in vitro diagnosis of autoimmune diseases, particularly systemic lupus erythematosus.

SUMMARY OF THE INVENTION

The present invention provides a uniform method for producing clinically important diagnostic reagents by non-covalently binding negatively charged polymeric compounds to the surface of polystyrene latex particles through methylated serum albumin. In accordance with one aspect of the invention, non-autoagglutinating latex particles sensitized with negatively-charged polymeric compounds are produced by non-covalently linking the polymeric compounds to water-soluble protein coated latex particles, through substantially methylated bovine serum albumin also adsorbed onto the particles.

Most polymeric compounds with a strong negative charge can bind to the matrix formed by the protein coating and the adsorbed methylated albumin. Suitable polymeric compounds include nucleic acids, negatively-charged proteins, and negatively charged polysaccharides; and suitable water-soluble proteins are albumins, particularly bovine serum albumin.

In one embodiment, an albumin, bovine serum albumin, and methylated bovine serum albumin are allowed to adsorb either sequentially, or coincidentally to polystyrene latex beads. The latex beads are washed and stored in a preservative solution. It is believed that the adsorption of the methylated serum albumin permits a nuclear component to non-covalently bind to the latex, creating a particle capable of agglutinating in the presence of autoimmune antibodies. Suitable nuclear components include chromatin, ribonuclear protein and deoxyribonuclear protein, deoxyribonucleic acid (DNA) and ribonucleic acid. When the nuclear component is native DNA, the relative viscosity in a buffer is between about 1.2 and 4.0, preferably between about 2.5 and 3.2. Native DNA sensitized particles are suitable for the in vitro diagnosis and screening of autoimmune diseases, particularly systemic lupus erythematosus. DNA from chicken blood, calf thymus, herring sperm or salmon testes may be utilized. If necessary, the relative viscosity is lowered by ultrasonication.

When a reagent specifically suitable for the detection of systemic lupus erythematosus is desired, a suitable method comprises the following steps:

(i) combining 1 volume of a concentrated suspension of polystyrene latex beads in a buffer, preferably 10 g/100 ml (w/v), with 0.2 volumes of from 10 micrograms/ml to 100 mg/ml bovine serum albumin in solution, preferably 33.3 mgs/ml and stirring for about 3 to 24 hours;

(ii) adding 0.5 volumes of from 10 micrograms/ml to 50 mg/ml methylated bovine serum albumin, preferably 33.3 mg/ml, in solution to the combination and stirring for about 3 to 24 hours;

(iii) mixing in 10 volumes of from 50 micrograms/ml to 5000 micrograms/ml, preferably 200 micrograms/ml, chicken blood, native deoxyribonucleic acid in solution, the deoxyribonucleic acid preferably having a relative viscosity of about 2.8, and stirring for about 3 hours;

(iv) washing the beads by centrifugation to separate the beads from unbound albumins or deoxyribonucleic acid; and (v) storing the washed beads in suspension, which may also contain preservatives, such as a detergent and a bacteriostatic agent.

Another aspect of the invention is a polystyrene latex reagent capable of agglutinating in the presence of circulating anti-nuclear antibodies. The reagent includes latex particles coated with a mixture of water-soluble albumin and substantially methylated serum albumin, to which is non-covalently bound a native DNA. The DNA has a relative viscosity between about 1.2 and 4.0, preferably from 2.5 to 3.2, and most preferably about 2.8, in a pH 6.8, 0.002 molar sodium phosphate buffer containing 0.2% w/v sodium chloride and 0.01% w/v thimerosal. The latex particles have an average diameter of about 0.05 to 1.1 microns, preferably 0.6 microns.

DETAILED DESCRIPTION OF THE INVENTION AND PREFERRED EMBODIMENT

A preferred method for the manufacture of a deoxyribonucleic acid (DNA) sensitized latex particles is as follows: native DNA, purified from chicken blood, was obtained commercially from Calbiochem-Behring, La Jolla, Calif. It was dissolved at 1 mg/ml in pH 6.8, 0.002 molar sodium phosphate buffer, which contained 0.2% w/v (grams per 100 ml) sodium chloride and 0.01% w/v thimerosal as preservative. The relative viscosity of the DNA solution was then measured. If the relative viscosity at 25° C. is greater than 4.0, the DNA is ultrasonically treated to reduce the viscosity. The preferred relative viscosity is between 2.5 and 3.2, although values somewhat higher or lower will give workable reagents. The DNA is put aside until it is needed.

The term "relative viscosity of DNA" indicates the ratio of the DNA's kinematic viscosity at 1 mg/ml in comparison to the solubilizing buffer's kinematic viscosity both measured at 25° C. The particular viscosity measuring means was a Cannon—Fenske Viscometer size 100, available from the Induchem Lab Glass Co., Roselle, N.J., but other means are acceptable. The ultrasonication, when needed, was accomplished with a Lab-Line ® Ultratip ® Labsonic system available from Lab-Line Instruments, Melrose Park, Ill. Other means of reducing viscosity are acceptable, but milder treatments are preferred to minimize breakage and separation of the DNA strands.

One volume of uniform polystyrene latex particles, 10% w/v and approximately 0.6 microns in diameter, is mixed with 0.3 volumes of 0.002 molar sodium phosphate buffer, pH 6.8, containing 0.01% thimerosal as preservative. Although 0.6 microns is the preferred particle size, other sizes ranging from 0.5 microns to 1.1 microns have been successfully used, although extremely small particles were difficult to wash and didn't provide optimal sensitivity. To the buffer/latex mixture is added 0.5 volumes of a 33.3 mg/ml solution of bovine serum albumin (BSA) in water. This entire mixture is stirred for a period of time ranging from about 3 to 24 hours. Bovine serum albumin is the preferred water-soluble protein for the initial coating of the particles, but other proteins, such as albumins, particularly human serum albumin, are also acceptable.

After the stirring, the BSA-latex is washed by centrifugation 3 times at about 20,000×g for 10 minutes and each time resuspended in one volume of 0.002 molar sodium phosphate buffer, pH 6.8. Anywhere from 0 to 3 centrifugations are done, with the preferred method calling for 3 centrifugations. To the resuspended mixture is added 0.5 volume of a 33.3 mg/ml solution of methylated bovine serum albumin in water, and the mixture is allowed to stir for 3 to 24 hours.

The BSA has been used in concentrations as low as 10 microgram/ml or as high as 100 mg/ml. The methylated BSA has been used in concentrations as low as 10 microgram/ml or as high as 50 mg/ml. At higher concentrations, washing by centrifugation is almost always necessary. It should be noted that both albumins may be added simultaneously; however, the preferred method is as described above.

The methylated bovine serum albumin may be prepared according to the paper of Mandell & Hershey, Anal. Biochem., 1, 66 (1960), or purchased commercially from Sigma Chemical Co., St. Louis, Mo., and Calbiochem, San Diego, Calif. The methylation does not have to be complete, but should be sufficient to render the material substantially water-soluble and salt insoluble.

At this time, a determination of the amount of material bound to the latex may be undertaken. A suitable technique is the Folin-Ciocalteu method of Lowry, which is used to analyze the supernatant from the centrifugation. Testing has shown that anywhere from 5 to 99% of the albumins is recovered in the supernatant, the actual amount depending on the original concentration of the proteins and the conditions of adsorbance.

The final albumins-latex complex is diluted with 0.002 molar sodium phosphate buffer, pH 6.8, containing 0.01% w/v thimerosal as preservative, to 5X the original volume of the 10% w/v latex particle suspension. To this is added 10 volumes of the previously prepared DNA solution at 200 ug/ml in 0.002 molar sodium phosphate buffer, pH 6.8, containing 0.2% sodium chloride and 0.01% w/v thimerosal as preservative. This total mixture is stirred for three hours, although this can be reduced to less than one hour or increased to 24 hours or more. The DNA solution can contain as much as 5000 micrograms/ml or as little as 50 micrograms/ml and the sodium chloride concentration can range from 0 to 0.9% or more.

After the appropriate time of stirring, the sensitized latex particles are washed by centrifugation in 0.002 molar sodium phosphate, pH 6.8 containing 0.2% w/v sodium chloride and 0.01% w/v thimerosal. Washing is not absolutely necessary, especially at lower DNA concentrations, but the preferred method calls for three washing steps. Final resuspension is done in 0.002 molar sodium phosphate, pH 6.8, which contains 0.2% w/v sodium chloride, 0.01% w/v thimerosal and 0.2% w/v Brij 58, a polyoxyethylene ether. Brij 58 is a non-ionic detergent that apparently enhances reactivity and promotes stability. Several other non-ionic detergents such as Brij 99 and Brij 30, commercially available from Sigma Chemical Co., St. Louis, Mo., can also be utilized. Ionic detergents, such as the Zwitterionic detergent, Zwittergent 3-12, a sulfabetaine, which is commercially available from Calbiochem-Behring, La Jolla, Calif., can also be added to the final suspending medium. Additionally, sodium phosphate is not the only acceptable buffer, for example, sodium maleate, tris (hydroxymethyl) aminomethane, and other buffers, at pH's ranging from about 6.0 to 8.0, have been successfully utilized.

The binding of DNA to the latex particles is shown indirectly by the fact that not all the DNA is recoverable in the supernatant fluid obtained after the final centrifugation. The quantity of bound DNA can be measured indirectly by the diphenylamine method. The amount found in the supernatant fluid seems to depend on the amount of methylated serum albumin adsorbed to the latex, as well as on the total amount of DNA added. Under the conditions described above, about 55-60% of the DNA is recovered in the supernatant, which approximately corresponds to the adsorbance of 80 micrograms DNA per ml. The maximum adsorbance of DNA occurs at a concentration in the final mixture of about 100 micrograms/ml, and as long as the conditions for the adsorption of the methylated bovine serum albumin remain constant, the same amount of DNA should be bound even if the final reaction mixture contains more DNA than 100 micrograms/ml. A reduction in the amount of methylated bovine serum albumin adsorption will concomitantly reduce the amount of DNA adsorbed to the latex. If the final reaction mixture contains less DNA than 100 micrograms/ml, then the amount of adsorbed DNA will be reduced.

The sensitized latex beads are routinely analyzed in a spectrophotometer to ascertain the amount of solids. The latex beads are diluted in a buffer and the absorbancy is measured at 650 nm. This analysis helps ensure the reagent's quality from batch to batch.

The sensitized particles were tested with various human sera to determine their ability to agglutinate in the presence of antibodies reative to native DNA as follows:

One drop of serum was placed on a black slide containing a 1 gram per 100 ml suspension of the native DNA-sensitized latex particles. The drops were gently mixed with an applicator stick for 10-15 seconds and then the entire slide tilted from side to side for about 2 minutes or more. The slide was then placed on a flat surface and visually studied for the presence of agglutination.

In one study involving 189 sera, effectiveness of latex particles sensitized with DNA was demonstrated as a diagnostic screening reagent for systemic lupus erythematosus. Of the 189 sera, 91 sera were apparently normal, while 98 sera had significant antinuclear antibody (ANA) titer as determined by other techniques. The ANA titer sera consisted of two groups. One group of 61 sera had high DNA binding, i.e., greater than 20% as determined by radioassay. The remaining 37 sera exhibited low DNA binding, i.e., less than 20% as determined by radioassay. It is believed that sera containing greater than 20% DNA binding come from patients suffering from systemic lupus erythematosus, whereas sera with lower DNA binding probably suffer from one of the related diseases.

Of the 61 sera with high DNA binding, 51 caused agglutination of the native DNA sensitized latex particles, whereas only one of the 37 sera with lower DNA binding and none of the apparently normal sera caused agglutination. These results indicate the utility of the test for screening purposes, particularly for systemic lupus erythematosus.

Various sources of DNA can be utilized with good results in practicing the present invention, particularly for the detection of ANA positive sera. DNA isolated by well-known methods from chicken blood, calf thymus, herring sperm and salmon testes, all with varying relative viscosities, give acceptable sensitized latex reagents. However, one preparation of DNA with a relative viscosity of about 4.0 caused auto-agglutination to occur after the latex beads had been sensitized. Although the cause of this is not completely understood, it is believed that the DNA cross-links with the latex particles, causing the agglutination. Mild ultrasonification at 180 watts of power on the Lab-Line sonicator reduced the molecular weight, as indicated by a reduction in relative viscosity and resulted in an acceptable reagent. Another native DNA preparation, this having a relative viscosity of less than 1.2, also gave an unacceptable reagent. The apparent cause, while again not completely understood, was that very little DNA bound to the latex surface, rendering the latex particles non-reactive with almost all sera, including ANA positive sera from systemic lupus erythematosus patients. For a reagent specific for systemic lupus erythematosus diagnosis, the preferred DNA is so-called native DNA, naturally occuring double-stranded DNA.

In addition to DNA, other polymeric compounds can be be bound to the latex particles, if these compounds contain sufficient negative charges. The terms "polymeric compounds" are intended to indicate large organic compounds, such as the nucleic acids, DNA and ribonucleic acid, as well as proteins and polysaccharides. Nucleic acids are generally negatively charged because of the many phosphate moieties along the backbone. A negatively charged protein that has been bound to latex particles in accordance with the present invention is porcine pepsin, which is composed of a large number of acidic, dicarboxylic amino acid and relatively few basic amino acids. Dextran sulfate, a polysaccharide, has also been successfully bound to latex particles, its negative charge is apparently due to the presence of a large number of sulfate groups attached to glucose residues, a primary repeating unit of the compound.

Various cell nuclear components can similarly be bound to latex particles adsorbed with methylated bovine serum albumin. In addition to nucleic acids, nuclear components include ribonuclear protein, deoxyribonuclear protein and the complex material, chromatin. Examples of techniques for the isolation and purification of these latter materials can be found in the treatise by L. S. Hnilicia, entitled "Structure and Biological Functions of Histones," CRC Press, Cleveland (1972).

An illustrative example of the reagent preparation in accordance with the present invention is as follows:

To 1 volume of 10% w/v latex of approximately 0.6 micron diameter is added 0.3 volume of 0.002 molar sodium phosphate, pH 6.8, containing 0.01% w/v thimerosal as preservative. To this is added 0.2 volume of 33.3 mg/ml bovine serum albumin solution in water and the mixture is stirred overnight. Then 0.5 volume of 33.3 mg/ml methylated bovine serum albumin is added and stirring again allowed to continue overnight. After the volume is adjusted to 5X the original volume with 0.002 molar sodium phosphate, pH 6.8, containing 0.01% w/v thimerosal, 10 volumes of 200 micrograms/ml chicken blood DNA in 0.002 molar sodium phosphate, pH 6.8, containing 0.2% w/v sodium chloride and 0.01% w/v thimerosal (as preservative) are added and allowed to mix for three hours. Washing is accomplished by centrifugation 3 times and the final reagent is resuspended in 10 volumes of 0.002 molar sodium phosphate, pH 6.8, containing 0.2% w/v sodium chloride, and 1% w/v Brij 58 and 0.01% thimerosal as preservatives.

From the foregoing, it will be appreciated that the utilization of water-soluble protein coated latex particles adsorbed with methylated serum albumin, made in accordance with the present invention, allows binding of negatively charged polymeric compounds to the latex particles. These sensitized particles are suitable for diagnostic testing with agglutination techniques and have minimal tendencies towards auto-agglutination. Further, methods of making and using a reagent for the in vitro diagnosis of auto-immune antibodies with latex particles sensitized with nuclear components, and specifically, a systemic lupus erythematosus screening agent composed of articles sensitized with native DNA, are provided.

Although the invention has been described in detail, it will be understood by one of ordinary skill in the art that various modifications can be made without departing from the spirit and scope of the invention. Accordingly, it is not intended that the invention be limited except as by the appended claims.

I claim:

1. A method for producing stable sensitized polystyrene latex particles useful as a diagnostic reagent in immunological procedures, the method comprising the steps of:
   (i) coating a polystyrene latex particle with a water-soluble protein;
   (ii) adsorbing a substantially methylated serum albumin onto the particle to form a matrix on the surface of the particle; and
   (iii) non-covalently binding a substantially negatively-charged, polymeric compound, having antigenic sites, to the matrix whereby a sensitized particle is made;
   wherein a mixture of sensitized particles in solution agglutinates in the presence of antibodies capable of binding antigenic sites of the polymeric compound, but does not exhibit significant auto-agglutination tendencies.

2. The method of claim 1 wherein the coating occurs by adsorption.

3. The method of claim 1 wherein the coating and adsorbing steps are coincident.

4. The method of claim 1 wherein the water-soluble protein is an albumin.

5. The method of claim 4 wherein the water soluble albumin is bovine serum albumin or human serum albumin.

6. The method of claim 1 wherein the negatively-charged polymeric compound is selected from the group consisting of nucleic acids, negatively charged polysaccharides, negatively charged proteins, and mixtures thereof.

7. The method of claim 6 wherein the nucleic acid is deoxyribonucleic acid.

8. The method of claim 1 wherein the water-soluble protein is bovine serum albumin, the methylated albumin is methylated bovine serum albumin, and the polymeric compound is deoxyribonucleic acid.

9. A method of making an immunological reagent for the in vitro diagnosis of rheumatic, autoimmune diseases, the method comprises adsorbing a water-soluble albumin and a substantially methylated bovine serum albumin onto surfaces of polystyrene latex beads, non-covalently binding a nuclear component to the methylated bovine serum albumin on the beads' surfaces, whereby the beads are sensitized with the nuclear component, and placing the beads in a preservative suspension, wherein the sensitized beads do not agglutinate in the presence of normal serum, but agglutinate in the presence of serum containing significant amounts of autoimmune antibodies.

10. The method of claim 9 wherein the water soluble albumin is adsorbed onto the beads' surfaces before the methylated bovine serum albumin.

11. The method of claim 9 wherein the water soluble albumin is human serum albumin or bovine serum albumin.

12. The method of claim 9 wherein the nuclear component is selected from the group consisting of chromatin, ribonuclear protein, deoxyribonuclear protein, and mixtures thereof.

13. The method of claim 9 wherein the nuclear component is selected from the group consisting of deoxyribonucleic acid, ribonucleic acid and mixtures thereof.

14. The method of claim 13 wherein the deoxyribonucleic acid in a buffer exhibits a relative viscosity greater than about 1.2 and less than about 4.0.

15. The method of claim 14 wherein the deoxyribonucleic acid exhibits a relative viscosity from about 2.5 to about 3.2.

16. The method of claim 13 wherein the deoxyribonucleic acid is isolated from chicken blood, calf thymus, herring sperm or salmon testes.

17. The method of claim 13 wherein prior to the binding of the deoxyribonucleic acid the relative viscosity of the deoxyribonucleic acid is adjusted by ultrasonication, whereby breakage and separation of strands in the deoxyribonucleic acid is minimized.

18. A method for producing a reagent capable of agglutinating an aliquot of serum from a patient suffering from serum lupus erythematosus, the method comprising the steps of:
   (i) combining 1 volume of a concentrated suspension of polystyrene latex beads, with 0.2 volumes of from about 10 micrograms/ml to 100 mg/ml bovine serum albumin in solution, and stirring;
   (ii) adding 0.5 volumes of from about 10 micrograms/ml to 50 mg/ml methylated bovine serum albumin in solution, and stirring;

(iii) mixing in about 10 volumes of from about 50 micrograms/ml to about 5000 micrograms/ml, native deoxyribonucleic acid in solution, the deoxyribonucleic acid (DNA) preferably having a relative viscosity of about 1.2 to about 4.0, and stirring;

(iv) washing the beads by centrifugation to separate the beads from unbound albumins or deoxyribonucleic acid; and (v) storing the washed beads as a suspension, containing preservatives.

19. The method according to claim 18 wherein the suspension of polystyrene latex beads has a concentration of about 10 grams/100 ml, the solution of bovine serum albumin has a concentration of about 33.3 mgs/ml, the solution of methylated bovine serum albumin has a concentration of about 33.3 mgs/ml, and the solution of DNA has a concentration of about 200 micrograms/ml.

20. The method according to claim 18 wherein the relative viscosity of the deoxyribonucleic acid is from about 2.5 to about 3.2.

21. The method according to claim 20 wherein the relative viscosity of the deoxyribonucleic acid is about 2.8.

22. The method according to claim 18 wherein the preservatives are a detergent and a bacteriostatic agent.

23. A latex bead made according to the method of claims 1, 8, 9 or 18.

24. A reagent for determining the presence of autoimmune antibodies in human serum comprising latex particles, having an average diameter from about 0.05 microns to about 1.1 microns, coated with a mixture of water-soluble albumin and substantially methylated bovine serum albumin, to which is non-covalently bound native deoxyribonucleic acid, the deoxyribonucleic acid exhibiting a relative viscosity between about 1.2 and 4.0 in a pH 6.8, 0.002 molar sodium phosphate buffer containing 0.2 grams sodium chloride and 0.01 grams thimerosal per 100 mls of the buffer.

25. The reagent of claim 24 wherein the water-soluble albumin is human serum albumin or bovine serum albumin.

26. The reagent of claim 24 wherein the diameter of the particles is about 0.6 microns.

27. The reagent of claim 24 wherein the relative viscosity of the deoxyribonucleic acid is from about 2.5 to about 3.2.

28. The reagent of claim 27 wherein the relative viscosity of the deoxyribonucleic acid is about 2.8.

29. The reagent of claim 28 wherein the deoxyribonucleic acid is isolated from chicken blood, salmon testes, herring sperm or calf thymus.

30. A method of testing in vitro for the presence of anti-native deoxyribonucleic acid antibodies in human fluids which comprises placing about one drop of human serum on a slide, adding one drop of a 1 gram per 100 mls suspension of the reagent of claim 24, tilting the slide for a time sufficient to allow agglutination, and observing the mixture for the presence of agglutination.

* * * * *

UNITED STATES PATENT AND TRADEMARK OFFICE
CERTIFICATE OF CORRECTION

PATENT NO. : 4,351,824
DATED : September 28, 1982
INVENTOR(S) : Harris I. Lehrer It is certified that error appears in the above-identified patent and that said Letters Patent is hereby corrected as shown below:

At Column 4, line 10, after the words "containing 0.01%" insert --w/v--.

At Column 4, line 63, after the words "containing 0.2%" insert --w/v--.

Signed and Sealed this

First Day of March 1983

[SEAL]

Attest:

Attesting Officer

GERALD J. MOSSINGHOFF

Commissioner of Patents and Trademarks